US012673038B2

(12) United States Patent
Kainz et al.

(10) Patent No.: US 12,673,038 B2
(45) Date of Patent: Jul. 7, 2026

(54) ANTIMYCOTIC METHOXYFLAVONE AND FLUCONAZOLE COMBINATION FOR INHIBITING CRYPTOCOCCUS

(71) Applicant: Karl-Franzens-Universität Graz, Graz (AT)

(72) Inventors: Katharina Kainz, Graz (AT); Andreas Zimmermann, Graz (AT); Didac Carmona-Gutierrez, Graz (AT); Frank Madeo, Graz (AT)

(73) Assignee: Karl-Franzens-Universität Graz, Graz (AT)

( * ) Notice: Subject to any disclaimer, the term of this patent is extended or adjusted under 35 U.S.C. 154(b) by 1092 days.

(21) Appl. No.: 17/629,546

(22) PCT Filed: Jul. 23, 2020

(86) PCT No.: PCT/EP2020/070807
§ 371 (c)(1),
(2) Date: Jan. 24, 2022

(87) PCT Pub. No.: WO2021/013930
PCT Pub. Date: Jan. 28, 2021

(65) Prior Publication Data

US 2022/0273610 A1 Sep. 1, 2022

(30) Foreign Application Priority Data

Jul. 23, 2019 (EP) .................................... 19187928

(51) Int. Cl.

| | |
|---|---|
| ***A61K 31/352*** | (2006.01) |
| ***A01N 43/16*** | (2006.01) |
| ***A61K 31/4174*** | (2006.01) |
| ***A61K 31/4196*** | (2006.01) |
| ***A61K 45/06*** | (2006.01) |

(52) U.S. Cl.
CPC ............ *A61K 31/352* (2013.01); *A01N 43/16* (2013.01); *A61K 31/4174* (2013.01); *A61K 31/4196* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2005/0249803 A1 | 11/2005 | Udell | |
| 2010/0015255 A1 | 1/2010 | Green et al. | |

FOREIGN PATENT DOCUMENTS

| | | | | |
|---|---|---|---|---|
| CN | 1836657 A | | 9/2006 | |
| CN | 105669625 A | * | 6/2016 | .......... A61K 31/352 |
| CN | 105669625 | | 5/2018 | |
| WO | WO2005039292 | | 5/2005 | |

OTHER PUBLICATIONS

Machine Translation of 105669625 B Specification, Translated by Patent Translate Espacenet.org on Jan. 14, 2025, 77 pages (Year: 2018).*
Machine Translation of CN105669625 A, Translated by Patent Translate Espacenet.org on Apr. 3, 2025, 74 pages specification, 14 pages claims. (Year: 2016).*
Whitney et al. "Treatment Principles for Candida and Cryptococcus" Cold Spring Harb Perspect Med 2015, 5, 6, a024158, 1-12. DOI: 10.1101/cshperspect.a024158 (Year: 2015).*
Lima at. al. "Anti-Candida and anti-Cryptococcus evaluation of 15 non-alkaloidal compounds from Pterogyne nitens" Asian Pac J Trop Biomed 2016, 6, 10, 841-845. DOI: 10.1016/j.apjtb.2016.08.003 (Year: 2016).*
Alves Abrahao et al: "Avaliacao dos Efeitos Farmacologicos e Toxicologicos do Extrato Etanolico, Fase Cloroformica e Flavonoide de Praxelis clematidea (griseb.) R.M. King & H. Robinson (Asteraceae)" , Thesis, Jan. 1, 2015 (Jan. 1, 2015), pp. 1-176, XP55623234.
Aurangzeb Hasan et al: "Structure Activity Relationship Studies of Some Potent Antifungal Flavones, 4-Thioflavones and 4-Iminoflavones", Asian Journal of Chemistry, Jan. 1, 2012 (Jan. 1, 2012), pp. 4361-4364, XP55623222.
Chavi Yenjai et al: "Bioactive flavonoids from Kaempferia parviflora", Fitoterapia, vol. 75, No. 1, Jan. 1, 2004 (Jan. 1, 2004), pp. 89-92, XP55188871.
Ernestina Almada-Ruiz et al: "Fungicidal potential of methoxylated flavones from citrus for in vitro control of Colletotrichum gloeosporioides , causal agent of anthracnose disease in tropical fruits : Fungicidal potential of methoxylated flavones from citrus", Pest Management Science, vol. 59, No. 11, Jun. 18, 2003 (Jun. 18, 2003) , pp. 1245-1249, XP55622766.
European Search Report and Search Opinion received for EP Application No. 19187928.7, mailed on Sep. 30, 2019, 21 pages.
International Preliminary Report on Patentability received for PCT Patent Application No. PCT/EP2020/070807, mailed on Feb. 3, 2022, 10 pages.
International Search Report and Written Opinion received for PCT Patent Application No. PCT/EP2020/070807, mailed on Sep. 28, 2020, 13 pages.
J. A. Del Rio et al: "Changes in the Levels of Polymethoxyflavones and Flavanones as Part of the Defense Mechanism of Citrus sinensis (Cv. Valencia Late) Fruits against Phytophthora citrophthora", Journal of Agricultural and Food Chemistry, vol. 52, No. 7, Apr. 1, 2004 (Apr. 1, 2004), pp. 1913-1917, XP55622778.

(Continued)

*Primary Examiner* — Jennifer A Berrios
*Assistant Examiner* — Sophia Reilly
(74) *Attorney, Agent, or Firm* — Workman Nydegger

(57) ABSTRACT

The present invention relates to methods and means for inhibiting or preventing the growth of fungal cells with at least one flavone selected from the group consisting of 5-methoxyflavone, 2'-methoxyflavone, 7-methoxyflavone, 3',4',5,7-tetrametoxyflavone, 3',4',5',5,6,7-hexymethoxyflavone, 7,8-benzoflavone and 5,6-benzoflavone for inhibiting or preventing the growth of a fungal cell, wherein said flavone is used in combination with at least one further antimycotic compound selected from the group of azoles, both in an amount to exhibit a synergistic effect compared to the separate use of said flavone and said antimycotic compound.

12 Claims, 18 Drawing Sheets

(56) References Cited

OTHER PUBLICATIONS

Li Liu et al: "Structure-Activity Relationship of Citrus Polymethoxylated Flavones and Their Inhibitory Effects on Aspergillus niger", Journal of Agricultural and Food Chemistry, vol. 60, No. 17, Apr. 20, 2012 (Apr. 20, 2012), pp. 4336-4341, XP55622816.
Sayed Alam et al : "Synthesis and Biological Activity of 7-Benzyloxy and 7-Methoxy Flavone", Pak. J. Sci. Res., Jan. 1, 2007 (Jan. 1, 2007), pp. 80-84, XP55623213.
Silva et al: "Growth contra I of different *Fusarium* species by selected flavones and flavonoid mixtures", Mycological Research, Elsevier, GB, vol. 102, No. 5, May 1, 1998 (May 1, 1998), pp. 638-640, XP022451470.
Ting Wu et al: "Antifungal action and inhibitory mechanism of polymethoxylated flavones from Citrus reticulata Blanco peel against Aspergillus niger", Food Control., vol. 35, No. 1, Jan. 1, 2014 (Jan. 1, 2014), pp. 354-359, XP55622751.
Tomas-Barberan FA et al: "Antifungal epicuticular methylated flavonoids from Helichrysum nitens", Phytochemistry, Pergamon Press, GB, vol. 27, No. 3, Jan. 1, 1988 (Jan. 1, 1988), pp. 753-755, XP026621018.
Vargas Irasema et al:"Antimicrobial And Antioxidant Compounds in the Nonvolatile Fraction of Expressed Orange Essential Oil". Journal of Food Protection, International Association for Food Protection, US, vol. 62, No. 8, Aug. 1, 1999 (Aug. 1, 1999) , pp. 929-932, XP009080545.
Weidenborner et al : "Antifungal spectrum of flavone and flavanone tested against 34 different fungi", Mycological Research, Elsevier, GB, vol. 101, No. 6, Jun. 1, 1997 (Jun. 1, 1997), pp. 733-736, XP022443577.
Xue Li et al: "Unusual Flavones from Primula macrocalyx as Inhibitors of OATI and OAT3 and as Antifungal Agents against Candida rugosa", Scientific Reports, vol. 9, No. 1, Jun. 25, 2019 (Jun. 25, 2019), XP55623084.
International Search Report issued in PCT/EP2020/070807 dated Sep. 28, 2020.
Xue Li, et al., "Unusual Flavones from Primula macrocalyx as Inhibitors of OAT1 and OAT3 and as Antifungal Agents against Candida rugosa", Scientific Reports, vol. 9, No. 1, Jun. 25, 2019.
Sayed Alam et al., "Synthesis and Biological Activity of 7-Benzyloxy and 7-Methoxy Flavone", Pak. J. Sci. Res., Jan. 1, 2007.
Fei Hu, et al., "Inhibitory effect of flavones from Ageratum conyzoides on the major pathogens in citrus orchard", Ying yong sheng tai xue bao, Oct. 1, 2002.
Bernini R, et al., "Obtaining new flavanones exhibiting antifungal activities by methyltrioxorhenium-catalyzed epoxidation-methanolysis of flavones", Tetrahedron, Elsevier Science Publishers, Amsterdam, NL, vol. 64, No. 32, Aug. 4, 2008.
Dal Piaz Fabrizio et al., "Phytochemistry of compounds isolated from the leaf-surface extract of Psiadia punctulate (DC.) Vatke growing in Saudi Arabia" Phytochemistry, Elsevier, Amsterdam, NL., vol. 155, Aug. 24, 2018.

* cited by examiner

ANTIMYCOTIC METHOXYFLAVONE AND FLUCONAZOLE COMBINATION FOR INHIBITING CRYPTOCOCCUS

TECHNICAL FIELD

The present invention relates to the field of antimycotics.

BACKGROUND ART

Fungal infections are rapidly developing into an increasing medical and socioeconomic problem. Both the number of infections as well as resulting deaths are increasing rapidly, so pandemic proportions may arise in the near future. The eukaryotic nature of the fungal cell and the resulting close relationship to human cells makes the search for new antifungal agents even more difficult.

Currently, there are only a very limited number of antimycotics on the market, which, however, sometimes cause serious side effects or are not as efficient as required. The effectiveness is increasingly limited as the incidence of resistance to it increases rapidly. Therefore, the search for new antifungal active substances is of major importance.

Weidenbörner et al. (Mycol. Res. 101 (1997): 733-736) found that flavone displays an antifungal effect against fungi including *Aspergillus* and *Fusarium* species.

An antifungal effect of flavones with methoxy substituents at certain positions has been described (Vargas et al., J. Food Prot. 62 (1999): 929-932; Almada-Ruiz et al., Pest Manag. Sci. 59 (2003): 1245-1249; Yenjai et al., Fitoterapia 75 (2004): 89-92; Del Rio et al., J. Agric. Food Chem. 52 (2004): 1913-1917; Liu et al., J. Agric. Food Chem. 60 (2012): 4336-4341; Wu et al., Food Control, 35 (2014): 354-359; CN 1 836 657 A; Li et al., Sci. Rep. 9 (2019): 9230; Tomas-Barberan et al., Phyto-chemistry 27 (1988): 753-755; Alam et al., Pak. J. Sci. Res. (2007): 80-84; Hasan et al., Asian J. Chem. (2012): 4361-4364; Silva et al., Mycol. Res. 102 (1998): 638-640; Abrahao et al., PhD Thesis, Universidad Federal de Paraiba, Brasil (2015), 1-176).

Formulations comprising more than one flavone derivative have been disclosed for uses other than antimycotics (US 2005/249803 A1; US 2010/015255 A1; WO 2005/039292 A1).

Besides the search of novel antimycotics, the search for so-called “potentiators”, i.e. substances that significantly increase the antifungal effect of antimycotics, has become increasingly important in recent years. Such substances may be able not only to increase the effect of antimycotics on fungal cells but also to broaden the effect of antimycotics on fungal cells whose viability cannot be effectively reduced using such antimycotics.

CN 105 669 625 A discloses a synergistic antifungal effect of certain flavonoids and fluconazole on *Candida albicans*. According to CN 105 669 625 A, 5-methoxyflavone does not show such synergistic effect.

It is an object of the present invention to provide methods, compounds and combination of compounds to effectively inhibit the growth of fungal cells ex vivo as well as in vivo and to affect their viability. Another object of the present invention is to provide compounds that are able to enhance the efficacy of antimycotics.

SUMMARY OF THE INVENTION

Thus, the present invention relates to the use of a flavone selected from the group consisting of 5-methoxyflavone, 2'-methoxyflavone, 7-methoxyflavone, 3',4',5,7-tetrametoxyflavone, 3',4',5',5,6,7-hexymethoxyflavone, 7,8-benzoflavone and 5,6-benzoflavone for inhibiting or preventing the growth of a fungal cell, wherein said flavone is used in combination with at least one further antimycotic compound selected from the group of azoles, both in an amount to exhibit a synergistic effect compared to the separate use of said flavone and said antimycotic compound.

Flavonoids are phytochemicals that are ubiquitous in plants and therefore also present in human food. Flavones, a class of flavonoids, have a 2-phenylchromen-4-one (2-phenyl-1-benzopyran-4-one) backbone and are commonly present in the food supply, mainly from spices, and red-purple fruits and vegetables. The flavones of the present invention are able to inhibit the growth of fungal cells so that the viability and the number of fungal cells is significantly decreased. It turned surprisingly out that the flavones of the present invention enhance the antifungal activity of other antimycotics. According to the present invention, said other antimycotics are selected from the group of azoles. Thus, the flavones of the present invention exhibit a synergistic effect with azoles. These antimycotic properties may not only be used for decreasing the number of viable fungal cells but also to prevent that fungal cells grow or reproduce.

The flavones of the present invention compromise fungal cell viability. This was exemplarily confirmed in the pathogenic yeast *Candida albicans* and *Candida glabrata*. Treatment of both planktonic cells and biofilms of *C. albicans* and *C. glabrata* with the flavones of the present invention resulted in a decreased proliferation of the pathogens as well as inhibition of biofilm formation. The antifungal potential of the flavones of the present invention could be demonstrated in vivo using a *Caenorhabditis elegans* infection model. In particular mono-substituted flavones, like 5-methoxyflavone, turned out to show good antimycotic properties.

Another aspect of the present invention relates to a composition comprising at least one flavone selected from the group consisting of 5-methoxyflavone, 2-methoxyflavone, 7-methoxyflavone, 3',4',5,7-tetrametoxyflavone, 3',4',5',5,6,7-hexymethoxyflavone, 7,8-benzoflavone and 5,6-benzoflavone and at least one further antimycotic compound selected from the group of azoles, both in an amount to exhibit a synergistic effect compared to the separate use of said flavone and said antimycotic compound.

Besides the antimycotic properties of the flavones of the present invention it turned surprisingly out that these flavones enhance the antifungal activity of other antimycotics.

Yet another aspect of the present invention relates to a composition according to the present invention or at least one flavone according to the present invention for the use in the treatment of a fungal infection in a human or animal, preferably mammalian, subject.

A further aspect of the present invention relates to a method for inhibiting or preventing the growth of a fungal cell comprising the step of contacting fungal cells with a composition of the present invention.

DESCRIPTION OF EMBODIMENTS

Figure 1A:
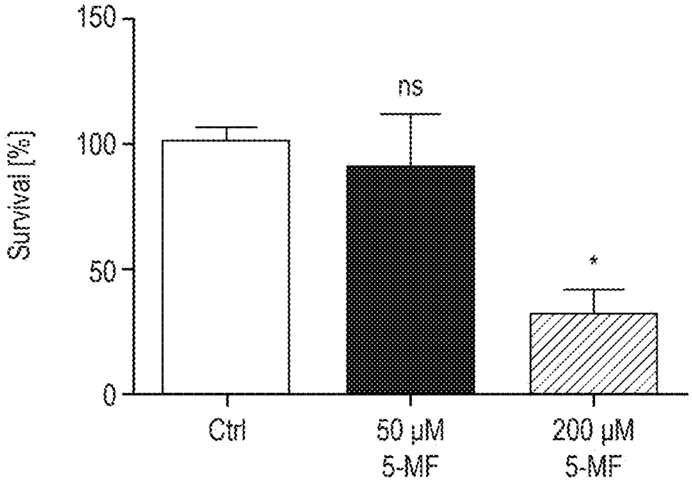
FIG. 1 shows the impact of 5-MF (5-methoxyflavone) on proliferation and survival of *Saccharomyces cerevisiae. S. cerevisiae* BY4741 cells were grown in SMD minimal media to mid-log phase and then treated with the indicated concentrations of 5-MF; control cells were treated with the same amount of solvent (DMSO). (A) Clonogenicity was assayed by plating 500 cells on YPD agar plates and colony forming units (CFUs) were counted to calculate survival rates. (B) Yeast cells were analyzed for cell death markers via AnnV/PI co-staining using flow cytometry. (C) The accumulation of reactive oxygen species was monitored by dihydrotethidium (DHE) to ethidium (Eth) conversion using flow cytometry. Assays in (A-C) were performed on day 3 after treatment. Data show mean±SEM of 3 independent experiments. Data was analyzed by one-way ANOVA and corrected for multiple comparison using a Bonferroni post-hoc test. ns: not significant, * $p<0.05$, * $p<0.001$, ** $p<0.0001$. (D) The MIC value of 5-MF for *S. cerevisiae* growth was examined following the standard CLSI protocol M27-A3 at OD490, and the untreated control was set to 100%. For dose-response data, sigmoidal curves were generated using nonlinear regression, and MIC-50 values (90.6±12.4 μM) were calculated from the whole dose-response curves. Data show mean±SEM of 4 independent experiments/curves.

The flavones of the present invention are selected from the group consisting of 5-methoxyflavone, 2'-methoxyflavone, 7-methoxyflavone, 3',4',5,7-tetrametoxyflavone, 3',4',5',5,6,7-hexymethoxyflavone, 7,8-benzoflavone and 5,6-benzoflavone. The flavones of the present invention are used in combination with at least one further antimycotic compound selected from the group of azoles, both in an amount to exhibit a synergistic effect compared to the separate use of said flavone and said antimycotic compound.

A "synergistic effect", as used herein, is defined as the response of two variables which is greater than the sum of both parts alone.

According to a preferred embodiment of the present invention, the flavone is 5-methoxyflavone.

Another aspect relates to the use of a flavone having formula (I)

(I)

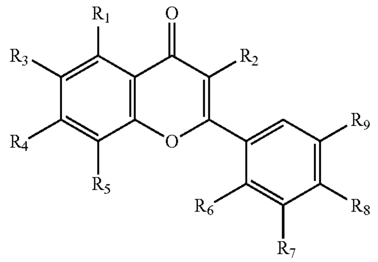

for inhibiting or preventing the growth of a fungal cell, wherein R1, R2, R3, R4, R5, R6, R7, R8 and R9 are independently from each other H, OCH3 or $OC_6H5$.

According to the present invention substituents $R_1$, $R_2$, $R_3$, $R_4$, $R_5$, $R_6$, $R_7$, $R_8$ and $R_9$ of the flavones of formula (I) may be independently from each other H, $OCH_3$ or $OC_6H_5$. In a particular preferred embodiment of the present invention one or more of substituents $R_1$, $R_2$, $R_3$, $R_4$, $R_5$, $R_6$, $R_7$, $R_8$ and $R_9$ may be $OCH_3$ or $OC_6H_5$, whereby $OCH_3$ is particularly preferred. Hence, it is preferred that at least one, preferably at least two, more preferably at least three, more preferably at least five, of substituents $R_1$, $R_2$, $R_3$, $R_4$, $R_5$, $R_6$, $R_7$, $R_8$ and $R_9$ are $OCH_3$.

In a particularly preferred embodiment, one, two, three, four, five, six, seven, eight or nine substituents are $OCH_3$ or $OC_6H_5$. In another embodiment of the present invention the substituents are H and $OCH_3$ or H and $OC_6H_5$, whereby substituents H and $OCH_3$ are mostly preferred. If substituents $R_1$, $R_2$, $R_3$, $R_4$, $R_5$, $R_6$, $R_7$, $R_8$ and $R_9$ are neither $OCH_3$ nor $OC_6H_5$ the substituents are by default H.

According to a preferred embodiment, $R_1$ or $R_2$ or $R_6$ or $R_6$ or $R_7$ and $R_8$ are $OCH_3$. Thereby it is preferred that the other substituents are H.

Although methoxy groups as substituents instead of H groups are mostly preferred, the substituents may also be phenoxy groups ($OC_6H_5$). In a particularly preferred embodiment the substituents $R_1$, $R_3$, $R_4$ and/or $R_5$, preferably $R_1$ and $R_3$ or $R_4$ and $R_5$, are $OC_6H_5$.

Methods for producing and/or isolating the flavones disclosed herein with the aforementioned substituents are well known in the art (Wagner and Farkas (1975) Synthesis of Flavonoids. In: Harborne, Mabry, Mabry (eds.) The Flavonoids, Springer, Boston (Mass., USA); Altemimi et al. (2017), Plants 6(4):42).

The flavones of the present invention influence the physiology and viability of fungal cells, so that these flavones may be used for inhibiting or preventing the growth of fungal cells. The flavones of the present invention may be used to control the growth of fungal cells wherever the presence of fungal cells is not desired. For instance, the flavones may be used in liquids, in suspensions, on surfaces or in any other composition. The flavones can also be used to inhibit the growth of fungal cells in food or feed. Also any kind of surface can be treated with the flavones of the present invention. Thus, the flavones of the present invention can be used non-therapeutically.

On the other side, the flavones of the present invention can also be used therapeutically in humans and animals, preferably mammals, in order to influence the viability and growth of fungal cells. Hence, the flavones of the present invention can be used in preventing and treating diseases caused by or associated with fungal cells.

The flavones of the present invention are able to control the growth and the viability of fungal cells, whereby the fungal cells are preferably filamentous or non-filamentous fungal cells.

According to a preferred embodiment of the present invention the non-filamentous fungal cell is of the class Saccharomycetes, preferably of the family Saccharomycetaceae, more preferably of the genus *Candida*.

The flavones of the present invention can modulate the growth of non-pathogenic as wells as of pathogenic fungal cells. Pathogenic fungal cells are of major importance so that it is particularly preferred that the fungal cell is a pathogenic fungal cell.

The fungal cells to be contacted with the flavones of the present invention may be single cells, cell colonies, biofilm-forming cells or biofilm cells, whereby biofilm-forming cells and biofilm cells are particularly preferred.

According to a preferred embodiment of the present invention the non-filamentous fungal cell is selected from the group consisting of *Candida albicans, Saccharomyces cerevisiae, Candida tropicalis, Candida dubliniensis, Candida parapsilosis, Candida kefyr, Candida guilliermondii, Candida inconspicua, Candida famata, Candida glabrata, Candida krusei, Candida lusitaniae, Candida auris, Cryptococcus neoformans*, and *Cryptococcus gattii*.

According to another preferred embodiment of the present invention the filamentous fungal cell is selected from the group consisting of *Aspergillus fumigatus, Aspergillus flavus, Aspergillus niger*, and *Aspergillus terreus*.

It turned surprisingly out that the flavones of the present invention are not only able to influence or prevent the growth of fungal cells but show significant synergistic effects on fungal cells when combined with other antimycotic compounds. It turned out that the flavones of the present invention show particular synergistic effects in regard to the growth and viability of fungal cells when used in combination with azoles.

Hence, according to the present invention, the at least one flavone is used in combination with at least one further antimycotic compound selected from the group of azoles. According to the present invention, the amount and/or concentration of the flavone and the azole is chosen in order to achieve a synergistic effect. Thus, the flavone of the present invention and the further antimycotic compound selected from the group of azoles are both used in an amount to exhibit a synergistic effect compared to the separate use of said flavone and said antimycotic compound.

Also disclosed herein is the use of a flavone having formula (I) in combination with at least one further antimycotic compound.

According to a preferred embodiment of the present invention the azole is an imidazole, a triazole or a thiazole.

According to a further preferred embodiment of the present invention the imidazole is selected from the group consisting of bifonazole, butoconazole, clotrimazole, econazole, fenticonazole, isoconazole, ketoconazole, luliconazole, miconazole, omoconazole, oxiconazole, sertaconazole, sulconazole and tioconazole.

According to another preferred embodiment of the present invention the triazole is selected from the group consisting of albaconazole, efinaconazole, epoxiconazole, fluconazole, isavuconazole, itraconazole, posaconazole, propiconazole, ravuconazole, terconazole and voriconazole.

According to a preferred embodiment of the present invention the triazole is abafungin.

According to a particularly preferred embodiment of the present invention the antimycotic compound is an azole selected from the group consisting of miconazole, ketoconazole, fluconazole and clotrimazole.

The at least one flavone of the present invention and optionally the at least one additional antimycotic compound can be used to prevent or inhibit the growth of fungal cells for various purposes. Hence, the aforementioned compounds can be applied in various ways depending where and how the growth and viability of fungal cells shall be inhibited or prevented. The at least one flavone may be applied on surfaces, added to suspensions and liquids or even incorporated into polymers, for instance.

The effective concentration of the flavones of the present invention is preferably from 1 to 500 μM, more preferably from 2 to 400 μM, more preferably from 5 to 300 μM. At theses concentrations the flavones of the present invention showed to be effective against fungal cells. Hence, it is particularly preferred to apply or administer the flavones of the present invention at these concentrations.

In combination with an antimycotic compound, namely with one or more azoles, the flavones and the further antimycotic compound(s) are preferably applied or administered at a concentration from 0.1 to 100 μM, prefer from 0.2 to 80 μM, more preferably from 0.5 to 50 μM.

According to a preferred embodiment of the present invention the flavones of the present invention are combined with an antimycotic compound selected from the group of azoles in a molar ratio of 2:1 to 100:1 (flavone:antimycotic compound).

Plants and parts thereof are often affected by fungal cells. Hence, the flavones of the present invention is preferably applied to a plant or parts thereof, in particular fruits or leaves.

According to a preferred embodiment of the present invention the plant is selected from the group consisting of wheat, barley, millet, oat, corn and rice.

Another aspect of the present invention relates to a composition comprising at least one flavone selected from the group consisting of 5-methoxyflavone, 2-methoxyflavone, 7-methoxyflavone, 3',4',5,7-tetrametoxyflavone, 3',4',5',5,6,7-hexymethoxyflavone, 7,8-benzoflavone and 5,6-benzoflavone and at least one further antimycotic compound selected from the group of azoles, both in an amount to exhibit a synergistic effect compared to the separate use of said flavone and said antimycotic compound.

Preferably, the composition of the present invention comprises 5-methoxyflavone.

It was surprisingly found that the flavones of the present invention show synergistic effects in combination with other antimycotic compounds, in particular with azoles. In addition thereto, it was found that antimycotic compounds which do not show an effect against certain fungal cells exhibit an antimycotic effect when combined with the flavones of the present invention.

Another aspect of the present invention relates to a composition comprising at least one flavone of formula (I) and at least one further antimycotic compound, wherein $R_1$, $R_2$, $R_3$, $R_4$, $R_5$, $R_6$, $R_7$, $R_8$ and $R_9$ are independently from each other H, $OCH_3$ or $OC_6H_5$.

According to a preferred embodiment, $R_1$ or $R_2$ or $R_6$ or $R_6$ or $R_7$ and $R_8$ are $OCH_3$.

In a particularly preferred embodiment, the substituents $R_1$, $R_3$, $R_4$ and/or $R_5$, preferably $R_1$ and $R_3$ or $R_4$ and $R_5$, are $OC_6H_5$.

According to the present invention, the antimycotic compound is selected from the group of azoles.

According to a preferred embodiment of the present invention the azole is an imidazole, a triazole or a thiazole.

According to a further preferred embodiment of the present invention the imidazole is selected from the group consisting of bifonazole, butoconazole, clotrimazole, econazole, fenticonazole, isoconazole, ketoconazole, luliconazole, miconazole, omoconazole, oxiconazole, sertaconazole, sulconazole and tioconazole.

According to another preferred embodiment of the present invention the triazole is selected from the group consisting of albaconazole, efinaconazole, epoxiconazole, fluconazole, isavuconazole, itraconazole, posaconazole, propiconazole, ravuconazole, terconazole and voriconazole.

According to a preferred embodiment of the present invention the triazole is abafungin.

According to a particularly preferred embodiment of the present invention the antimycotic compound is an azole selected from the group consisting of miconazole, ketoconazole, fluconazole and clotrimazole.

The composition of the present invention may be used for controlling the growth and viability of fungal cells in animals, preferably mammals, and humans. Thus, the composition of the present invention may comprise at least one pharmaceutically acceptable excipient which is mainly dependent from the route of administration and well known to a person skilled in the art and commonly used for antimycotic compositions.

Another aspect of the present invention relates to a composition of the present invention or at least one flavone as defined above for the use in the treatment of a fungal infection in a human or animal, preferably mammalian, subject.

According to one aspect, the present invention relates to a composition of the present invention for the use in the treatment of a fungal infection in a human or animal, preferably mammalian, subject.

It was surprisingly found that the composition of the present invention can be used as a medicament for treating or preventing fungal infections in humans and animals, preferably mammals.

The at least one flavone of the present invention is administered preferably to the human or animal, preferably mammalian, subject together or subsequently with at least one further antimycotic compound selected from the group of azoles.

In another aspect, the composition of the present invention is administered to the subject together or subsequently with at least one further antimycotic compound, preferably selected from the group of azoles.

According to a particularly preferred embodiment of the present invention the composition or the flavone and/or the at least one further antimycotic compound selected from the group of azoles are administered orally, topically or intravenously.

In one aspect, the composition of the present invention is administered orally, topically or intravenously.

The composition as well as the flavone of the present invention can be formulated for any kind of mode of delivery to the patient including oral, topical, by inhalation, intravenous or parenteral administration. Thus, depending upon chosen mode of administration, the composition and the flavone of the present invention can be formulated with common excipients, diluents or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone.

Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

For oral administration, the flavone and the further antimycotic compound may be present as a powder, a granular formulation, a solution, a suspension or an emulsion or may be presented as a bolus, electuary or paste.

Tablets containing the compounds of the present invention can include buffering agents such as calcium carbonate, magnesium oxide and magnesium carbonate. Tablets can also include inactive ingredients such as cellulose, pre-gelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatin capsules containing the compounds of the present invention can contain inactive ingredients such as gelatin, microcrystalline cellulose, sodium lauryl sulfate, starch, talc, and titanium dioxide and the like, as well as liquid vehicles such as polyethylene glycols (PEGs) and vegetable oil. Moreover, enteric-coated tablets or capsules are also provided and designed to resist disintegration in the stomach and dissolve in the more neutral to alkaline environment of the duodenum. Orally administered therapeutic compounds of the present invention can also be formulated for sustained release.

A sustained-release formulation can be designed to release the compounds of the present invention, for example, in a particular part of the intestinal or respiratory tract, possibly over a period of time. Coatings, envelopes, and protective matrices may be made, for example, from polymeric substances, such as polylactide-glycolates, liposomes, microemulsions, microparticles, nanoparticles, or waxes.

The flavones and the at least one further antimycotic compounds of the present invention can also be formulated as elixirs or solutions for convenient oral administration or as solutions appropriate for parenteral administration, for instance by intramuscular, subcutaneous, intraperitoneal or intravenous routes.

For parenteral administration, e.g. by injection, for example, bolus injection or continuous infusion, the compounds of the present invention may be presented in unit dose form in ampoules, pre-filled syringes, small volume infusion containers or in multi-dose containers. Preservatives can be added to help maintain the shelve life of the dosage form. The compounds of the present invention and other ingredients may form suspensions, solutions, or emulsions in oily or aqueous vehicles, and may contain formulatory agents such as suspending, stabilizing and/or dispersing agents.

It is particularly preferred to administer the flavones and compositions of the present invention topically or to mucosal surfaces such as the vagina, the rectum, eyes, nose and the mouth. For topical administration, the therapeutic agents may be formulated as is known in the art for direct application to a target area. For topical application creams, milks, gels, dispersion or microemulsions, lotions thickened to a greater or lesser extent, impregnated pads, ointments or sticks, aerosol formulations (e.g., sprays or foams), soaps, detergents, lotions or cakes of soap are particularly preferred. Other conventional forms for this purpose include wound dressings, coated bandages or other polymer coverings, ointments, creams, lotions, pastes, jellies, sprays, and aerosols.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. Topical applications may also comprise an adjuvant. Compositions for topical application to skin may include an adjuvant, solvent, or co-solvent to assist the flavone and optionally the additional antimycotic compounds with penetrating the outer dermal layers. An exemplary adjuvant, solvent, or co-solvent is dimethyl sulfoxide (DMSO).

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions pH 7.0-8.0.

Another aspect of the present invention relates to a method for inhibiting or preventing the growth of a fungal cell comprising the step of contacting fungal cells with at a composition as defined above.

Another aspect of the present invention relates to a method for inhibiting or preventing the growth of a fungal cell comprising the step of contacting fungal cells with at least one flavone as defined above.

According to a preferred embodiment of the present invention the at least one flavone is contacted together or subsequently with at least one further antimycotic compound as defined above.

EXAMPLES

Material & Methods

Yeast Strains, Fungal Strains and Growth Conditions

*Saccharomyces cerevisiae* and *Candida* strains were maintained in YPD media (10 g/L Yeast extract, 20 g/L Peptone, 40 g/L Pextrose/glucose). Experiments were performed in YPD media, in PRMI media (Sigma Aldrich, Germany) buffered with MOPS (TCI, Germany or ABCR, Germany) or SC media (1.7 g/L yeast nitrogen base (BD, Germany), 5 g/L ammonium sulfate (Roth, Germany)) supplemented with 20 g/L glucose (Applichem, Germany) and 30 mg/L proteinogenic amino acids (Serca, Germany) except for lysine (120 mg/L), leucine (200 mg/L), histidine (80 mg/L) as well as 30 mg/L adenine (Serca, Germany) and 320 mg/L uracil (Sigma Aldrich, Germany). Experiments with *Aspergillus* strains were done in PDB (Potatoe Dextrose Bouillon) media (BD, Germany). Agar (20 g/L; BD, Germany) was added to prepare solid media. For long time storage yeast strains in YPD were mixed 1:1 with 50% glycerol as antifreeze and stored at −80° C. *Aspergillus* strains were stored at −80° C. by collecting spores and mixing them with glycerol to achieve a final concentration of $2\times10^7$ spores/mL.

Yeast Survival and Cell Death Assays

Yeast strains were streaked on YPD agar plates and allowed to grow for two days at 28° C. or 30° C., plates were then stored for up to one week at 4° C. Starting from overnight cultures in YPD or SMD, respective media in deep-well plates (validation) or glass flasks (toxicity tests) were inoculated to an OD600 of 0.1. Cells were treated as indicated and incubated at 28° C. and 1000 rpm (deep-well plates) or 145 rpm (flasks).

For screen validation propidium iodide (PI) staining was used. Therefore, $\sim5\times10^6$ cells were harvested and stained with 100 ng/mL PI (Sigma, Germany) in PBS and incubated for 5 min in the dark. After staining cells were sedimented again and resuspended in PBS to avoid dye deposition. For each sample, at least 30,000 cells were analyzed using flow cytometry (LSRII Fortessa, BD; Ex: 488 nm, Em: 585 nm)

Survival upon treatment with substances or combinations was analyzed by plating serial dilutions of treated cultures onto YPD agar plates. Plates were incubated for two days at 28° C., colony forming units (CFUs) were counted and survival was calculated compared to the untreated control.

Accumulation of ROS was determined by dihydroethidium (DHE) staining as described for PI staining, using a 100 ng/mL DHE solution (Sigma, Germany) in PBS. After staining cells were sedimented again and resuspended in PBS to avoid dye deposition. For each sample, at least 30,000 cells were analyzed using flow cytometry (LSRII Fortessa, BD; Ex: 488 nm, Em: 585 nm).

Cell death markers were assessed by AnnexinV/PI co-staining. Therefore, 1-2×107 cells were harvested and treated with 3 μL lyticase (1,000 U/mL; Sigma, Germany) and 15 μL glucuronidase/arylsulfatase (4.5 U/mL; Roche, Austria) for sphaeroblastation (60 min at 28° C. and 145 rpm). Resulting sphaeroblasts were co-stained with AnnexinV (Roche, Austria) and PI (Sigma, Germany) and analyzed via flow cytometry, using an LSRII Fortessa (BD, Ex: 488 nm; Em: 695 nm for PI and 530 nm for FITC). At least 30,000 cells were analyzed for each sample.

In Vitro Antifungal Susceptibility Testing

Minimal Inhibitory Concentration

The minimal inhibitory concentration (MIC) was determined following the standard Clinical and Laboratory Standards Institute (CLSI) protocol M27 (Rex JH, and Clinical and Laboratory Standards Institute (2008). Reference method for broth dilution antifungal susceptibility testing of yeasts: approved standard, 3rd ed. National Committee for Clinical Laboratory Standards, Wayne, PA) for yeast strains or the standard CLSI protocol M38 (Clinical and Laboratory Standards Institute (2008). Reference method for broth dilution antifungal susceptibility testing of filamentous fungi. Clinical and Laboratory Standards Institute, Wayne, PA) for filamentous fungi.

For yeast strains media was inoculated with an overnight culture to an $OD_{600}$ of 0.001 ($1^{04}$ cells/mL). Serial dilutions of substances were added and cells were incubated at 37° C. without shaking for 48±1 h.

For filamentous fungi, ½ PDB media was inoculated with respective spores to a concentration of $4\times10^4$ spores/mL. Serial dilutions of substances were added and spores were incubated at 22° C. without shaking for three to four days.

MIC tests were performed in flat-bottom 96 well plates (Greiner Bio One, Austria) using 100 μL suspension per well sealed with gas-permeable foils. After incubation, OD490 values were measured using 96-well plate reader and growth capacity was analyzed by setting the corresponding control to 100%.

Biofilm Inhibition Concentration

The biofilm inhibition concentration (BIC) was determined as described in Delattin N et al. (J Antimicrob Chemother 69(2014): 1035-1044). In short, RPMI medium was inoculated with an overnight culture to an OD of 0.1, transferred to a U-bottom 96-well plate (MLS, Belgium) and treated with serial dilutions of substances. After the adherence phase (1 h, 37° C.), supernatant was removed, adherent cells were washed with PBS and fresh media (including substances) was added. Biofilms were then allowed to grow for 24 h at 37° C.

Formed biofilms were then analyzed for their metabolic activity. Therefore, *C. albicans* biofilm cells were treated with CTB (cell titer blue®; Promega, Germany), diluted 1:100 in PBS. After incubation for 1 h at 37° C. in the dark fluorescence intensity was measured using a 96 well plate reader (Ex: 535, Em: 590, sens 65). For *C. glabrata*, XTT (2H-Tetrazolium, 2,3-bis(2-methoxy-4-nitro-5-sulfophenyl)-5-[(phenylamino) carbonyl]-hydroxide; Sigma, Germany or ABCR, Germany) was used instead. Thereby, biofilm cells were treated with an XTT solution (0.25 mg/mL XTT+0.1 μM menadione in PBS) at 37° C. in the dark and $OD_{490}$ was measured.

Additionally, biofilm inhibition was determined by plating experiments. Therefore, grown biofilms were washed, biofilm cells were resuspended in PBS+1% Triton and serial dilutions were plated on YPD agar plates. Plates were incubated at 37° C. for one day and CFUs were counted.

As for MIC, biofilm inhibition was analyzed by setting the corresponding control to 100%.

Biofilm Eradication Concentration

To determine the biofilm eradication concentration (BEC), biofilms were grown as described above in the absence of substances. Pre-grown biofilms (24 h, 37° C.) were washed with PBS before adding fresh media and serial dilutions of substances. After incubation for 24 h at 37° C., metabolic activity of remaining biofilm cells was analyzed as described above.

Checkerboard Assay (Synergy Testing)

For synergy testing of different combinations, checkerboard assays were performed. Therefore, serial dilutions of two different compounds were combined for MIC, BIC or BEC testing as described above. Antifungal activity of substances alone or in combination was determined by setting the corresponding control to 100%.

In Vivo Antifungal Susceptibility Testing Using *Caenorhabditis elegans*

*C. elegans* Maintenance and Long-Time Storage

The *C. elegans* Δglp-4 Δsek-1 strain (generously provided by Valerie Defraine, Centre of Microbial and Plant Genetics, KU Leuven, Belgium) was used for in vivo testing of antifungal activity. Worms were maintained on NGM plates (nematode growth medium; 2.5 g/L Bacto Peptone, 3 g/L NaCl, 17 g/L agar, supplemented with 5 mg/L cholesterol, 1 mM $CaCl_2$, 1 mM $MgSO_4$ and 25 mM $KPO_4$ buffer pH 6.0), seeded with a thin layer of *E. coli* OP50, at 16° C. and worms were chunked onto fresh plates every three to four days.

For longtime storage, starved worms were harvested from plates, diluted 1:1 with 50% glycerol as an antifreeze and stored at −80° C.

Egg Collecting and Synchronization of *C. elegans*

Egg collecting was performed by bleaching according to Stiernagle T ("Maintenance of *C. elegans*". WormBook. doi: 10.1895/wormbook1.101 (2006)) and Porta-de-la-Riva M et al. JoVE 64(2012): e4019-e4019). In short, adult worms were collected from plates and treated with a bleaching solution (10 mL household bleach+5 mL 5M NaOH), thereby worms disintegrate and eggs are released. After vigorous shaking for 5 min, M9 medium (3 g/L $KH_2PO_4$, 6 g/L $Na_2HPO_4$, 5 g/L NaCl, supplemented with 1.25 mM MgSO4) was added and worms were immediately put on ice. After three washing steps, residual eggs were incubated in M9 medium over night at 16° C. on a tube roller. The next day, eggs were collected, transferred onto fresh NGM/OP50 plates and incubated at 25° C. for 3-4 days until nematodes have reached the L3/L4 stage prior to infection.

Infection with *C. albicans* and Efficacy Testing

Synchronized (L3/L4 stage) worms were collected, washed three times with M9 media and spotted onto prepared YPD plates with a thin layer of *C. albicans* SC5314. Nematodes were fed on YPD/*C. albicans* plates for of 2 h at 25° C. To remove residual yeast on the cuticula of the worms, nematodes were collected and washed several times with MilliQ water using a sterilized membrane (pore size~20 μM). Collected nematodes were then resuspended in growth medium (M9 medium supplemented with 10 μg/mL cholesterol, 100 μg/mL kanamycin and 75 μg/mL ampicillin) and diluted to a concentration of ~40 worms/750 μL.

For efficacy testing of compounds, 750 μL of the worm suspension were transferred into each well of a 24-well plate and substances were added at indicated concentrations (1% DMSO). Nematodes were immediately counted (t0) and survival was monitored over five days post infection by counting living worms.

Data Analysis

Presented data represent mean±s.e.m of at least three independent experiments. For dose-response experiments, sigmoidal curves were generated using non-linear regression (formula: Y=Bottom+(Top−Bottom)/(1+10^((Log IC50−X)*HillSlope))) and IC50 values were derived from the whole dose-response curves. Data were analyzed by one-way ANOVA and corrected for multiple comparison using a Bonferroni post-hoc test and a confidence level of 0.05. All data were analyzed using GraphPad Prism 6.

Example 1: 5-Methoxyflavone Inhibits Proliferation And Induces Necrotic Cell Death in *S. cerevisiae*

As many of the commercially available pharmaceuticals in general, the majority of antifungal drugs currently in use were derived from natural sources. For example, Amphotericin B (AMB), the "golden standard" for the treatment of serious fungal infections, is a product of the bacterium *Streptomyces nodosus*. Caspofungin and Micacfungin, two members of the echinocandin class of antifungal drugs, are synthesized by the fungi *Glarea lozoyenis* and *Coleophoma empetri*, respectively. In addition to natural compounds from microbial origin, substances derived from higher plants have gained increasing attention for drug development. Among them, compounds from the flavonoid superfamily have emerged as promising bioactive agents with therapeutical potential.

Figure 1B:
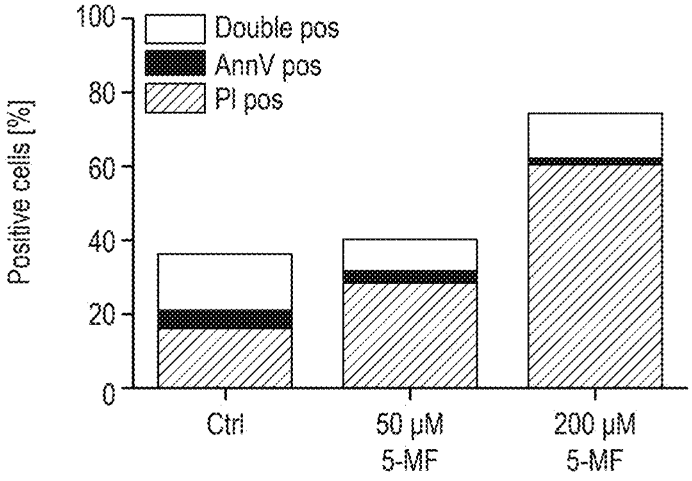
Figure 1C:
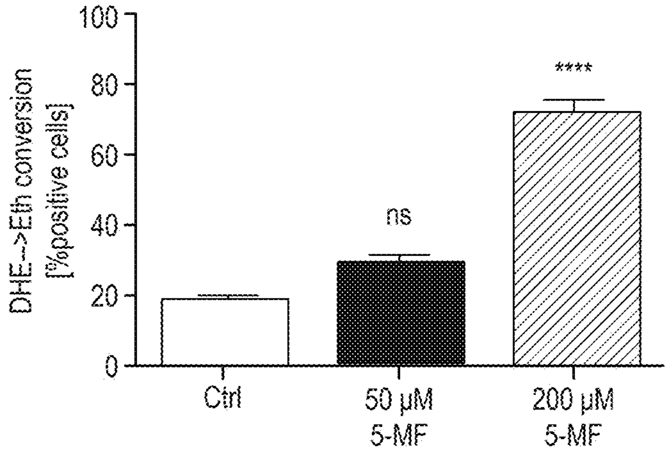

5-methoxyflavone (5-MF) was investigated regarding its ability to impact proliferation and viability of *S. cerevisiae*. Indeed, 5-MF (200 μM) strongly decreased yeast survival compared to the untreated control (31% vs. 100%), as determined by a clonogenic assay (FIG. 1A). In addition, AnnexinV/Propidium iodide (AnnV/PI) co-staining was performed to establish the cell death routine induced by 5-MF. AnnV binds to externalized phosphatidylserine and is thus considered a marker for apoptotic cell death whereas PI intercalates into the DNA of cells with a ruptured plasma membrane and is thus a marker for necrotic cells. Interestingly, 5-MF mainly increased the PI-positive fraction in a concentration-dependent manner, indicating that 5-MF-treated cells predominantly die via a necrotic cell death pathway (FIG. 1B). Furthermore, it was shown that 5-MF causes accumulation of reactive oxygen species (ROS) (FIG. 1C), suggesting an involvement of oxidative stress in the lethal process.

Figure 1D:
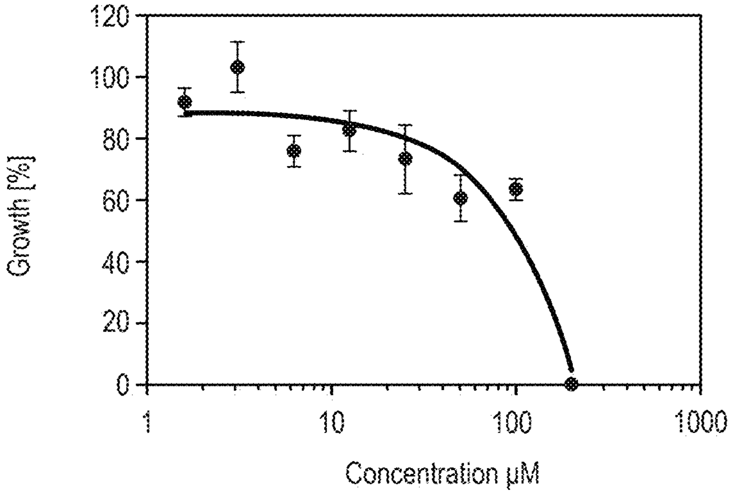

Finally, the effect of 5-MF on the growth of *S. cerevisiae* following the standard Clinical and Laboratory Standards Institute (CLSI) protocol M27-A3 for the determination of the minimal inhibitory concentration (MIC) was investigated. The MIC-50 value is defined as the concentration that is required to reduce the growth of planktonic cells by 50% compared to the control. 5-MF showed a dose-response curve in *S. cerevisiae* that yielded a MIC-50 value of 90.6±12.4 μM (FIG. 1D). Taken together, these data show clearly that 5-MF exhibits fungicidal activity.

Example 2: 5-MF Reduces Growth and Biofilm Formation in *Candida* ssp.

Fungal infections (FIs) are among the most rapidly growing socioeconomic and medical problems, calling for the urgent development of new antimycotics.

Figure 2A:
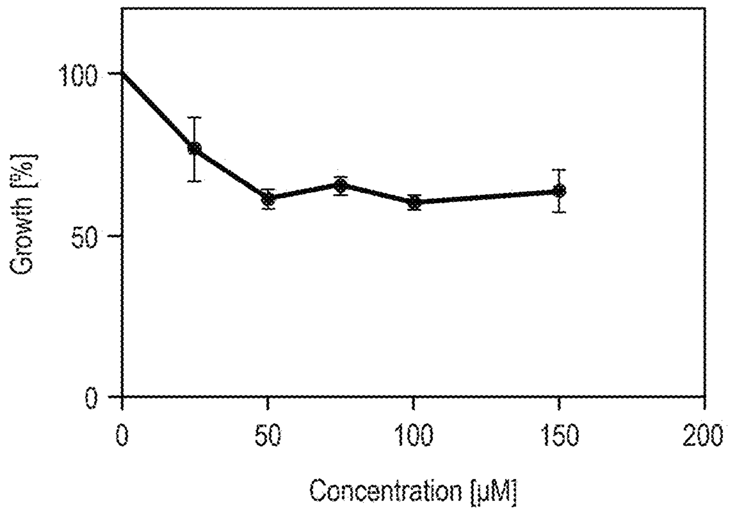
FIG. 2 shows that 5-MF inhibits proliferation and biofilm formation of *C. albicans* and *C. glabrata*. Antifungal activity was analyzed following the standard CLSI protocol M27-A3 (M27-A3; ISBN 1-56238-666-2; 2008; Vol. No. 14) at $OD_{490}$, and the untreated control was set to 100%. (A) Antifungal activity of 5-MF against *C. albicans* SC5314. Data represent means±SEM of 3 independent experiments. (B) Antifungal activity of 5-MF against *C. glabrata* BG2. For dose-response data, sigmoidal curves were generated using nonlinear regression and the MIC-50 values (201.6±35.6 μM) were derived from the whole dose-response curves. Data represent means±SEM of 6 independent experiments. (C, D) Anti-biofilm activity of 5-MF was analyzed using CTB-staining (*C. albicans*) or XTT-staining (*C. glabrata*) as described in Delattin N, et al. (Antimicrob Chemother. 69(2014): 1035-1044). For dose-response data, sigmoidal curves were generated using nonlinear regression and the BIC-50 values were derived from the whole dose-response curves. Data represent means±SEM of at least 3 independent experiments. The BIC-50 value of 5-MF for *C. albicans* SC5314 biofilms was calculated as 215.9±26.6 μM (C). The BIC-50 value of 5-MF for *C. glabrata* BG2 biofilms was calculated as 224.4±15.6 μM (D). (E) *C. glabrata* biofilms were washed, resuspended in PBS and plated on YPD agar plates. Colony forming units were counted and surviving biofilm cells were calculated compared to the untreated control. Data represent means±SEM of 6 independent experiments. Data were analyzed using one-way ANOVA and corrected for multiple comparison using a Bonferroni post-hoc test. ns: not significant, * $p<0.05$,  $p<0.01$, * $p<0.001$.
Figure 2B:
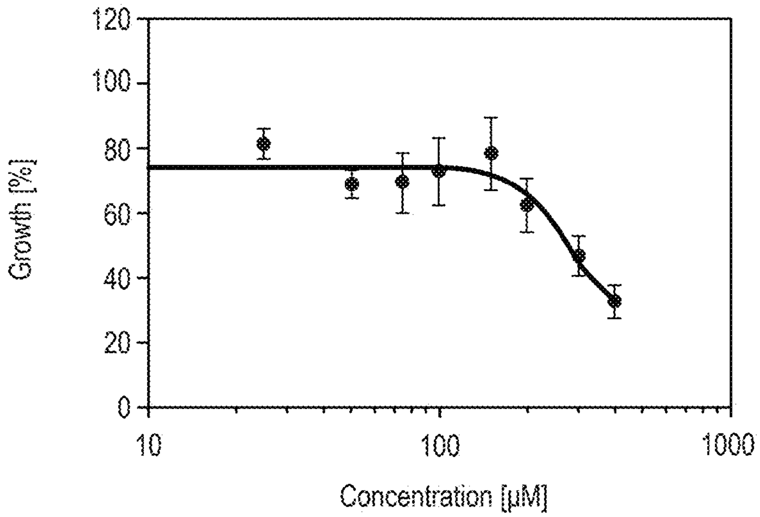

The results obtained in the model system *S. cerevisiae* (Example 1) showed 5-MF as a putative antifungal agent. Thus, the activity of 5-MF against *C. albicans*, the leading pathogen in regards to severe FIs, and *C. glabrata*, an emerging non-albicans *Candida* (NAC) species was investigated. For that purpose, the effect of 5-MF on planktonic cells of both *Candida* species following the standard CLSI protocol M27-A3 (M27-A3; ISBN 1-56238-666-2; 2008; Vol. 28 No. 14) to determine corresponding MIC values was tested. 5-MF reduced growth of planktonic *C. albicans* SC5314 cells at a concentration of 50 μM to about 60% compared to untreated cells (FIG. 2A). No further reduction in growth was observed with increasing concentrations of 5-MF, which precluded the generation of a sigmoidal dose-response curve and the calculation of a defined MIC-50 value. However, the obtained data clearly show that 5-MF is able to inhibit proliferation of *C. albicans* already at low concentrations. *C. glabrata* BG2, a *Candida* species closer related to *S. cerevisiae* than to other *Candida* species, showed a similar response as *S. cerevisiae* upon treatment with 5-MF, but yielded a higher MIC-50 value of 201.6±35.6 μM (FIG. 2B).

Next the potential of 5-MF to interfere with *C. albicans* SC5314 and *C. glabrata* BG2 biofilm formation was examined. As mentioned above, *Candida* species are able to form biofilms, multicellular communities known to convey protection to external physical and chemical challenges, including known antifungal compounds, and to act as a cellular storage for pathogen spreading. *Candida* biofilms were grown as previously described (Delattin N, et al. Antimicrob Chemother. 69(2014): 1035-1044) and treated with different concentrations of 5-MF.

Figure 2C:
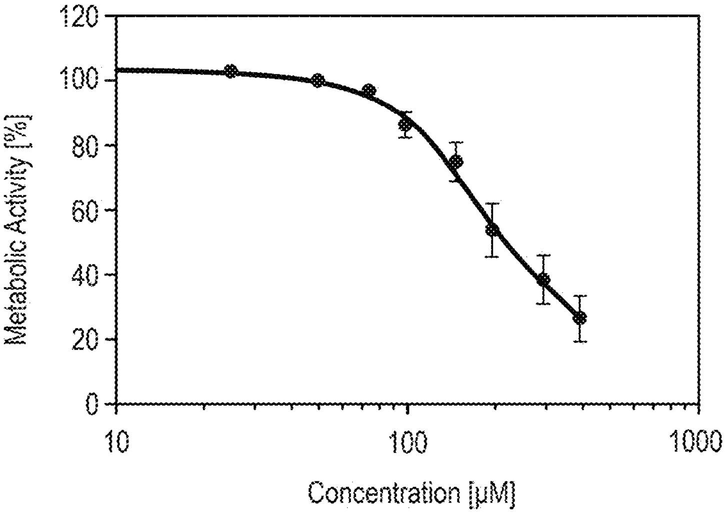
Figure 2D:
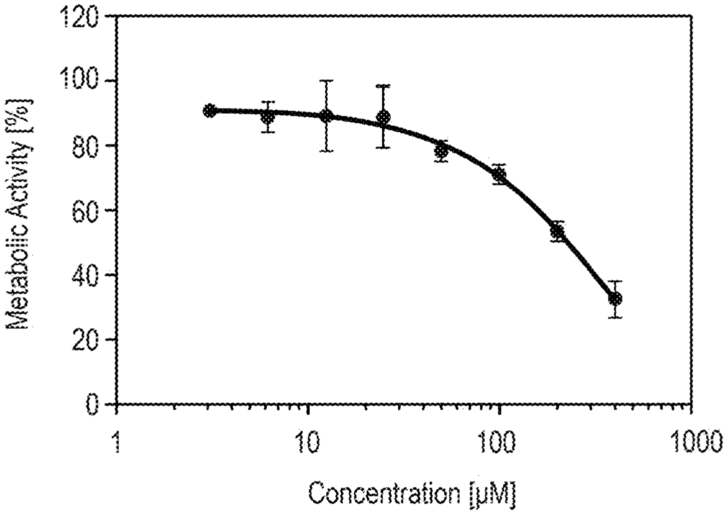
Figure 2E:
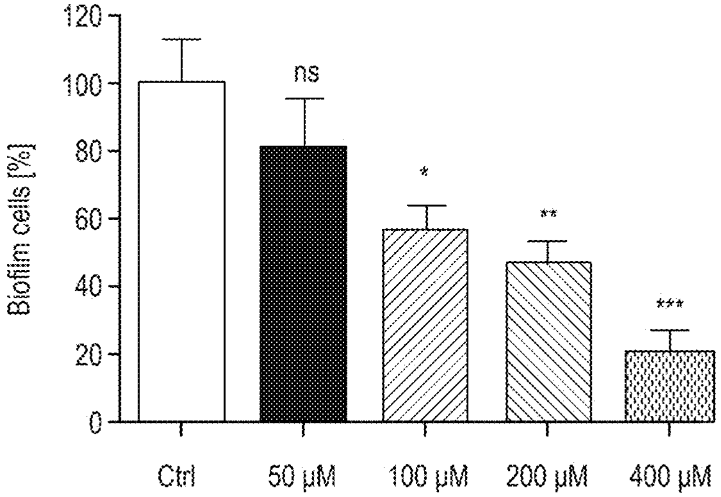

Biofilm inhibition was analyzed by monitoring the metabolic activity of *C. albicans* and *C. glabrata* biofilms via CTB (CellTiter-Blue® Promega)- and XTT-staining, respectively (Delattin N, et al. Antimicrob Chemother. 69(2014): 1035-1044). Conversion of CTB (a resazurin dye) into a fluorescent end product (resorufin) reflects active cell metabolism and is thus used to monitor cell viability. As *C. glabrata* is not able to convert CTB in a proper time period, XTT was used instead. Similar to CTB, XTT (a tetrazolium salt) is converted to a coloured formazan product when cells are metabolically active and thus considered viable. The BIC-50 value, the concentration that is required to inhibit biofilm formation by 50% compared to the untreated control, was calculated from the whole dose-response curves. 5-MF showed a clear biofilm inhibition in both *Candida* strains with similar BIC-50 values: 215.9±26.6 μM for *C. albicans* (FIG. 2C) and 224.4±15.6 μM for *C. glabrata* (FIG. 2D). In addition to determining the metabolic activity, *C. glabrata* biofilms were also plated on YPD agar plates to verify the actual cell titer within the biofilm. In accordance with the results obtained with XTT staining, the number of biofilm cells decreased in a concentration-dependent manner (FIG. 2E). Of note, these data were also quantitatively similar to those measured via XTT staining. Altogether, these in vitro data confirm the potential of 5-MF as a putative antifungal agent.

Example 3: 5-MF Combats *C. albicans* Infection in a *C. elegans* Infection Model To verify if the antifungal activity of 5-MF observed in vitro also holds true in vivo, the nematode model *Cae-*

Figure 3A:
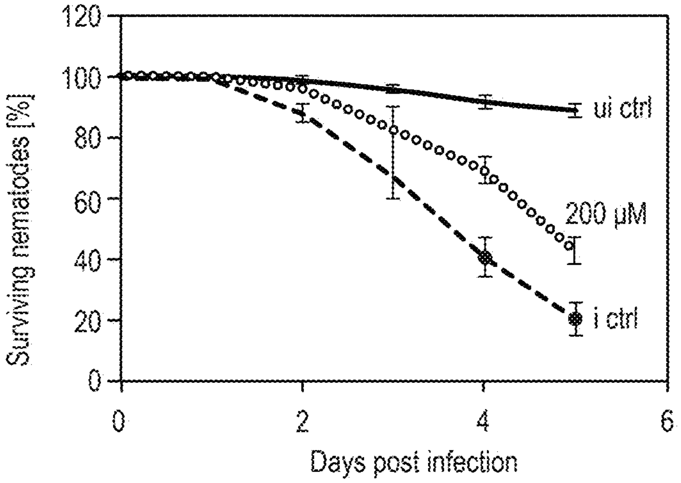
FIG. 3 shows that 5-MF promotes survival of infected nematodes in an in vivo model for *C. albicans* infection. Survival curves of non-infected (ui ctrl.) and infected (i ctrl.) nematodes treated or not with 5-MF are shown in (A), and the survival of living nematodes on day 5 is shown in (B). Synchronized *C. elegans* Δglp-4 Δsek-1 larvae were infected at the L4 stage as previously described (Delattin N, et al., Antimicrob Chemother. 69(2014): 1035-1044). 35-50 infected worms were then suspended in 750 μL growth medium (M9 buffer supplemented with 10 mg/L cholesterol, 100 mg/L kanamycin and 75 mg/L ampicillin) in separate wells of a 24-well plate with at least 3 wells for each condition. Worms were treated with 200 μM 5-MF or the corresponding volume of solvent (i ctrl) immediately after infection (single application). Worm survival was monitored daily over the period of five days. Additionally, the survival of non-infected worms (ui ctrl) was monitored as a control. Data show means±SEM of 5 independent experiments. In (B), worm survival is expressed as the percentage of viability at day 5 compared to day 0, with data analyzed using one-way ANOVA and corrected for multiple comparison using a Bonferroni post-hoc test.  $p<0.01$, ** $p<0.0001$.
Figure 3B:
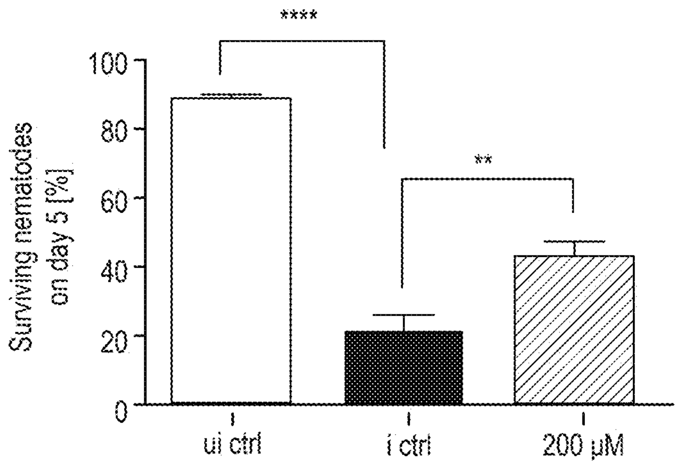

*norhabditis elegans* as a well-established model for bacterial and fungal infections was used. For that purpose, a mutant strain of *C. elegans* (*C. elegans* Δglp-4 Δsek-1) with enhanced vulnerability for *C. albicans* infections was used (Breger J, et al. PLOS Pathog. 3(2007): e18. doi: 10.1371/journal.ppat.0030018). For the infection assay, synchronized larvae were infected/fed with *C. albicans* as previously described (Delattin N, et al. Antimicrob Chemother. 69(2014): 1035-1044) and treated with 5-MF or the solvent alone (i ctrl) immediately after infection. In addition, a non-infected control (ui ctrl) was monitored in parallel, i.e. nematodes fed with *E. coli* OP50 (the standard food source for *C. elegans*) instead of *C. albicans*. Nematode survival was monitored daily over a time period of 5 days post infection (FIG. 3A). Indeed, 5-MF treatment conferred prolonged protection compared to the infected control. At day 5 post infection, only 20.6% of the worms were alive in the infected control, compared to 42.9% of worms treated with 200 μM 5-MF (FIG. 3B).

In summary, both in vitro and in vivo models show that 5-MF acts as an antimycotic agent with the potential of a broad antifungal spectrum. Altogether, the data show that 5-MF can be applied as a standalone antifungal compound.

Example 4: 5-MF Enhances the Antifungal Activity of Azoles

In vitro antifungal activity of 5-MF in combination with different azoles was analyzed by monitoring growth of yeast cells via $OD_{490}$ measurement, and the untreated control was set to 100%.

Figure 4A:
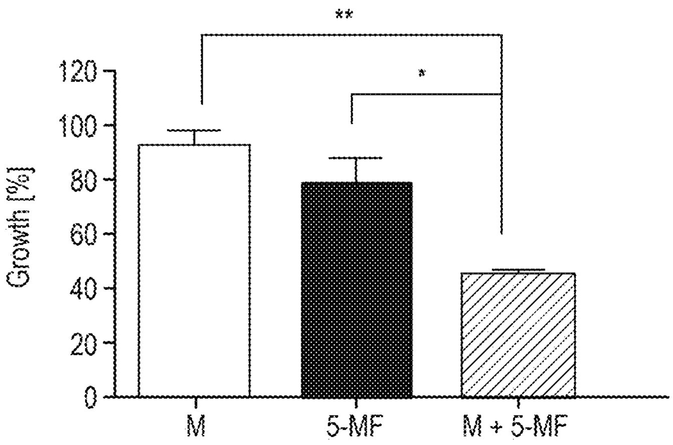
FIG. 4 shows the enhancement of the antifungal activity against *C. albicans* of azoles in the presence of 5-methoxyflavone (5-MF).

In vitro antifungal activity of 5-MF in combination with miconazole is shown in FIG. 4A. *C. albicans* cells were either treated with 0.4 μM miconazole (M) or 50 μM MF alone or in combination. Data represent means±SEM of 3 independent experiments.

Figure 4B:
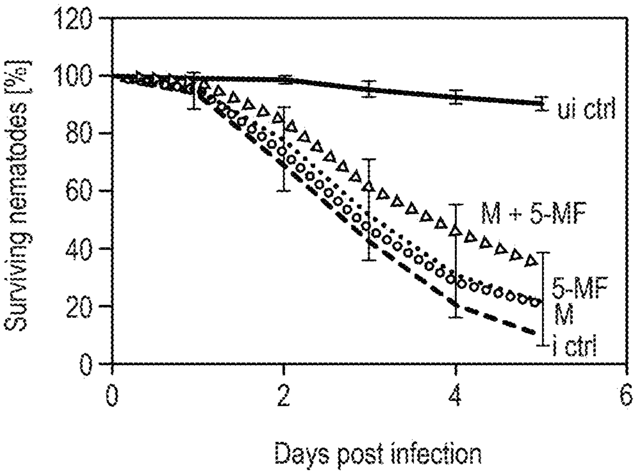
Figure 4C:
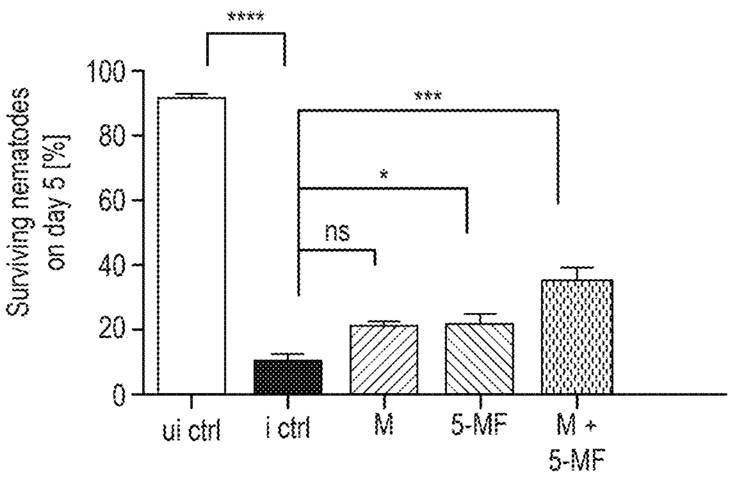

In vivo antifungal activity of 5-MF in combination with miconazole is shown in FIGS. 4B and C. Survival curves of non-infected (ui ctrl.) and infected (i ctrl.) nematodes treated or not with 5-MF or miconazole alone or in combination are shown in (B), and the survival of living nematodes on day 5 is shown in (C). Synchronized *C. elegans* Δglp-4 Δsek-1 larvae were infected at the L4 stage as previously described (Delattin N, et al. J Antimicrob Chemother. 69(2014): 1035-1044). 35-50 infected worms were then suspended in 750 μL growth medium (M9 buffer supplemented with 10 mg/L cholesterol, 100 mg/L kanamycin and 75 mg/L ampicillin) in separate wells of a 24-well plate with at least 3 wells for each condition. Worms were treated with either 50 μM 5-MF or 0.125 μM miconazole alone or in combination, or with the corresponding volume of solvent (i ctrl) immediately after infection (single application). Worm survival was monitored daily over the period of five days. Additionally, the survival of non-infected worms (ui ctrl) was monitored as a control. Data show means±SEM of 3 independent experiments. In (C), worm survival is expressed as the percentage of viability at day 5 compared to day 0.

Figure 4D:
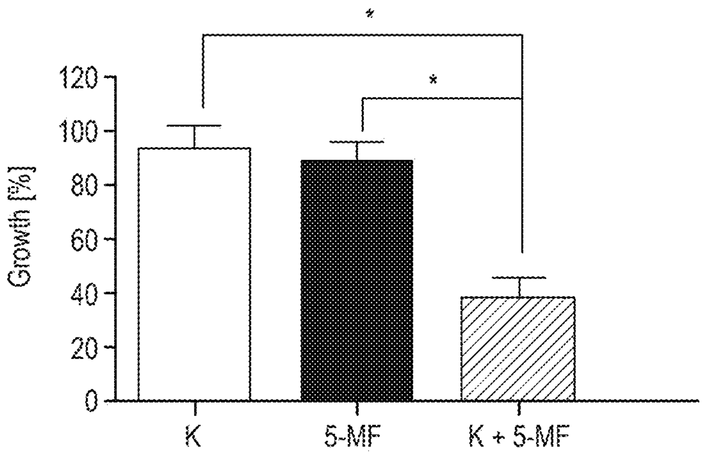

In vitro antifungal activity of 5-MF in combination with ketoconazole is shown in FIG. 4D. *C. albicans* cells were either treated with 3.9 μM ketoconazole (K) or 12.5 μM MF alone or in combination. Data represent means±SEM of 3 independent experiments.

Figure 4E:
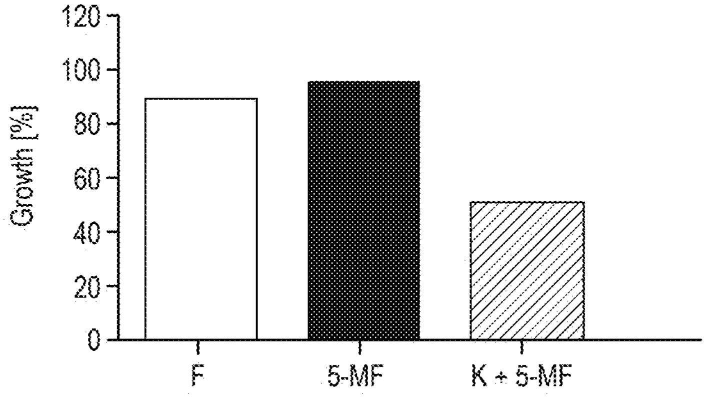

FIG. 4E shows that the combination of 5-MF with fluconazole results in a much higher inhibition of fungal cells. *C. albicans* cells were either treated with 1 μM fluconazole (F) or 12.5 μM MF alone or in combination. Data represent means of 2 independent experiments. Data were analyzed using one-way ANOVA and corrected for multiple comparison using a Bonferroni post-hoc test. ns: not significant, *p<0.05, p<0.01, *p<0.001, ****p<0.0001.

Figure 5A:
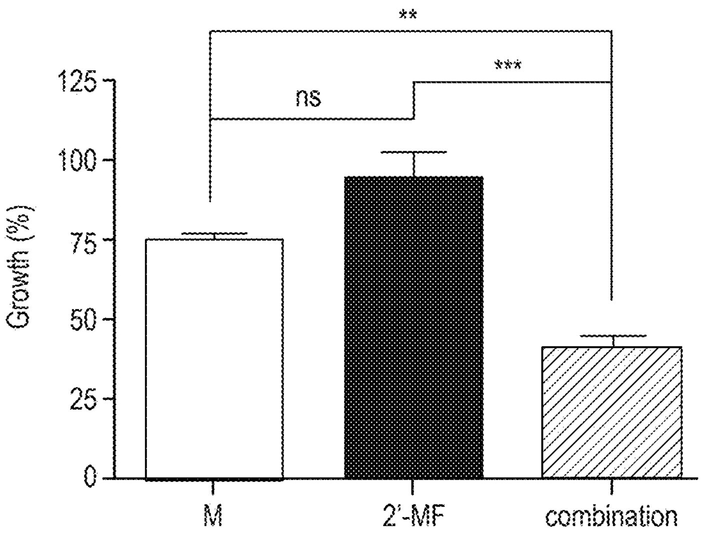
FIG. 5 shows the enhancement of the antifungal activity against *C. albicans* of azoles in the presence of 2'-methoxyflavone (2'-MF).
Figure 5B:
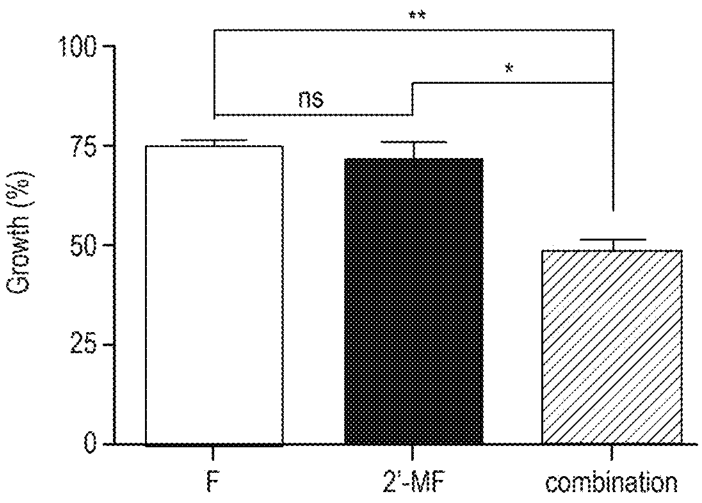
Figure 5C:
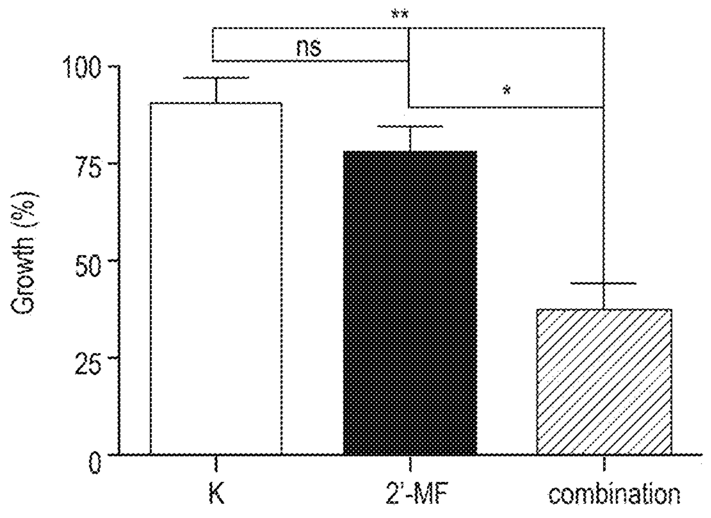
Figure 5D:
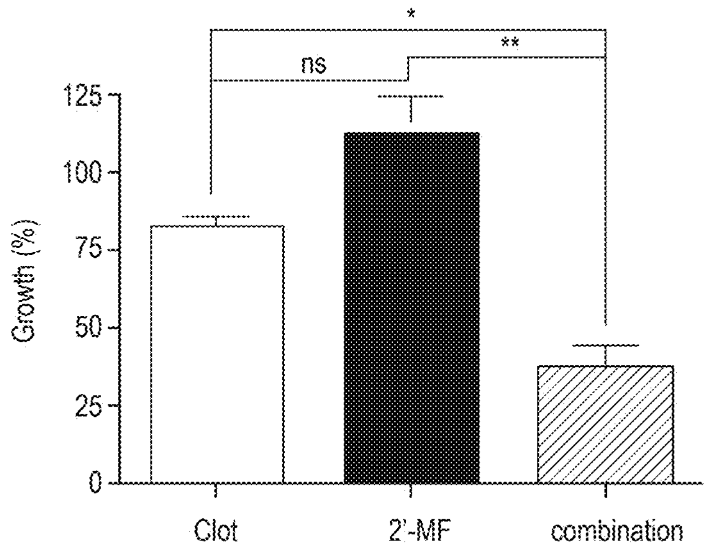

Example 5:2'-Methoxyflavone Enhances the Antifungal Activity of Azole Antimycotics In vitro antifungal activity of 2'-methoxyflavone (2'-MF) in combination with miconazole (M), fluconazole (F), ketoconazole (K) and clotrimazole (Clot) against *C. albicans* was analyzed by monitoring growth of yeast cells via $OD_{490}$ measurement, and the untreated control was set to 100%. Cells were either treated with 0.4 μM M or 25 μM 2'-MF alone or in combination (see FIG. 5A). Cells were either treated with 1 μM F or 6.25 μM 2'-MF alone or in combination (see FIG. 5B). Cells were either treated with 0.5 μM K or 6.25 μM 2'-MF alone or in combination (see FIG. 5C). Cells were either treated with 0.2 μM Clot or 25 μM 2'-MF alone or in combination (see FIG. 5D). Data represent means±SEM of at least 3 independent experiments. ns: not significant, *p<0.05, p<0.01, *p<0.001. (E-F) Preliminary data.

Figure 6A:
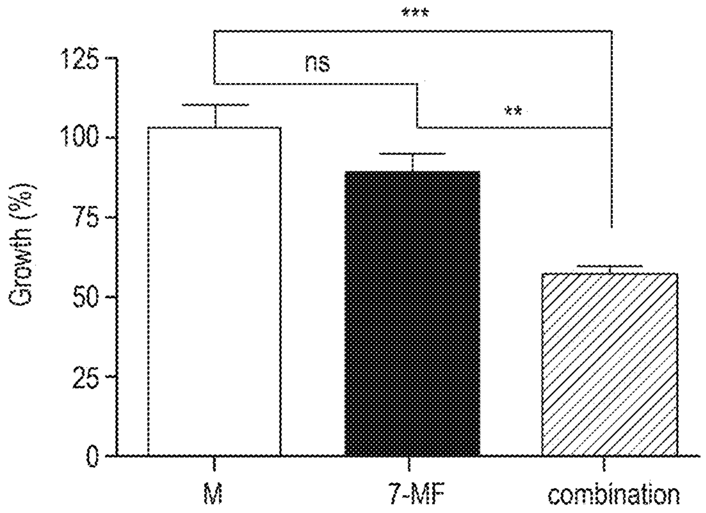
FIG. 6 shows the enhancement of the antifungal activity against *C. albicans* of azoles in the presence of 7-methoxyflavone (7-MF).
Figure 6B:
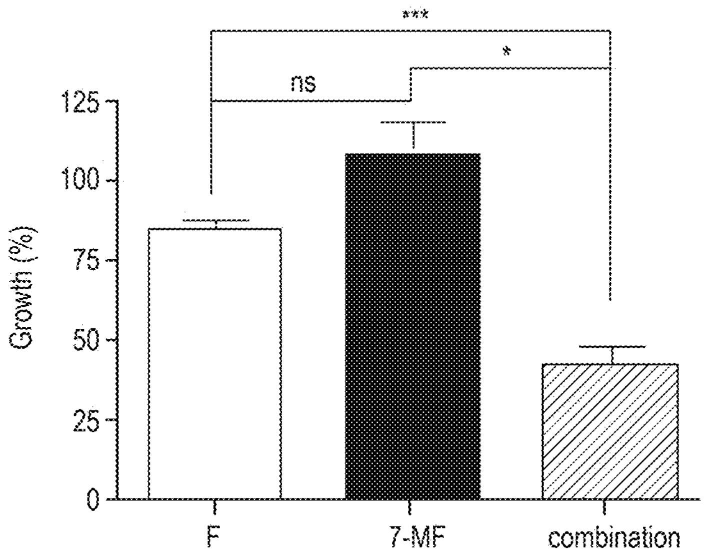
Figure 6C:
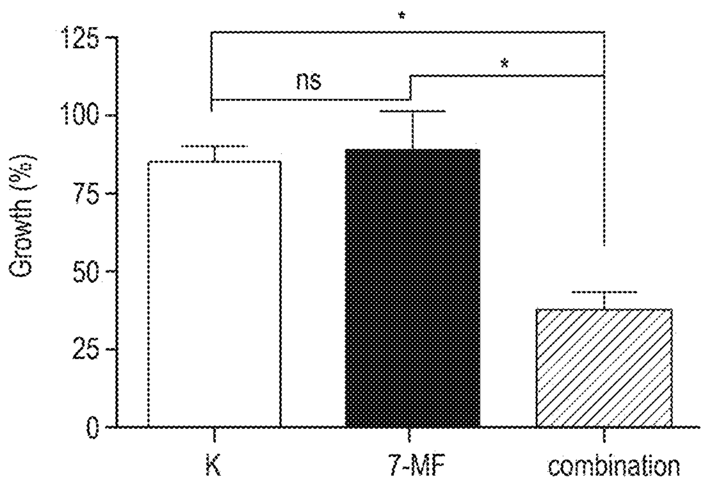
Figure 6D:
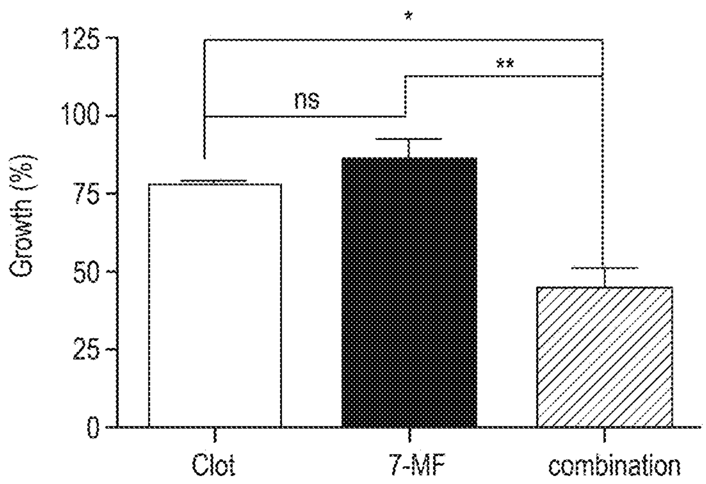

Example 6: 7-Methoxyflavone Enhances the Antifungal Activity of Azole Antimycotics In vitro antifungal activity of 7-methoxyflavone (7-MF) in combination with miconazole (M), fluconazole (F), ketoconazole (K), and clotrimazole (Clot) against *C. albicans* was analyzed by monitoring growth of yeast cells via OD490 measurement, and the untreated control was set to 100%. Cells were either treated with 0.4 μM M or 25 μM 7-MF alone or in combination (see FIG. 6A). Cells were either treated with 1 μM F or 50 μM 7-MF alone or in combination (see FIG. 6B). Cells were either treated with 0.5 μM K or 12.5 μM 7-MF alone or in combination (see FIG. 6C). Cells were either treated with 0.2 μM Clot or 25 μM 7-MF alone or in combination (see FIG. 6D). Data represent means±SEM of at least 3 independent experiments. ns: not significant, *p<0.05, p<0.01, *p<0.001.

Example 7: Benzoflavones Enhance the Antifungal Activity of Azole Antifungals

Figure 7A:
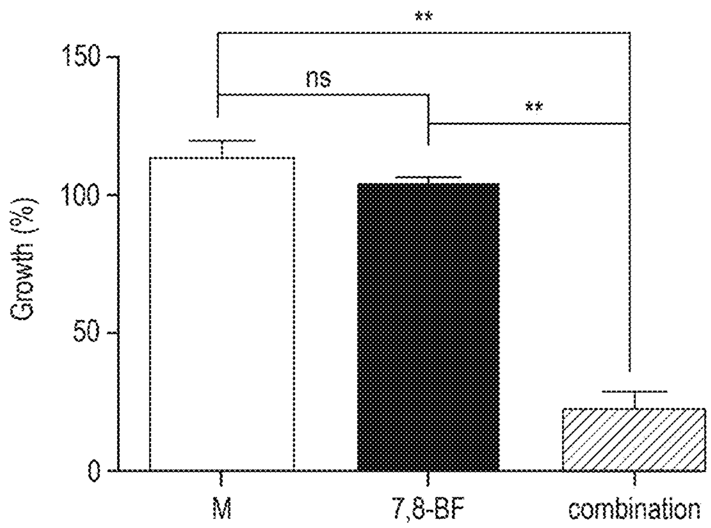
FIG. 7 shows the enhancement of the antifungal activity against *C. albicans* of azoles in the presence of 7,8-benzoflavone (7,8-BF) or 5,6-benzoflavone (5,6-BF).
Figure 7B:
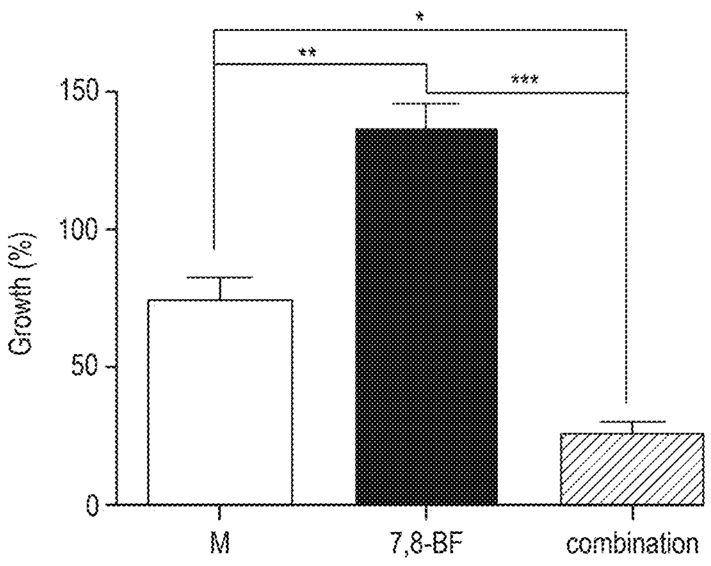
Figure 7C:
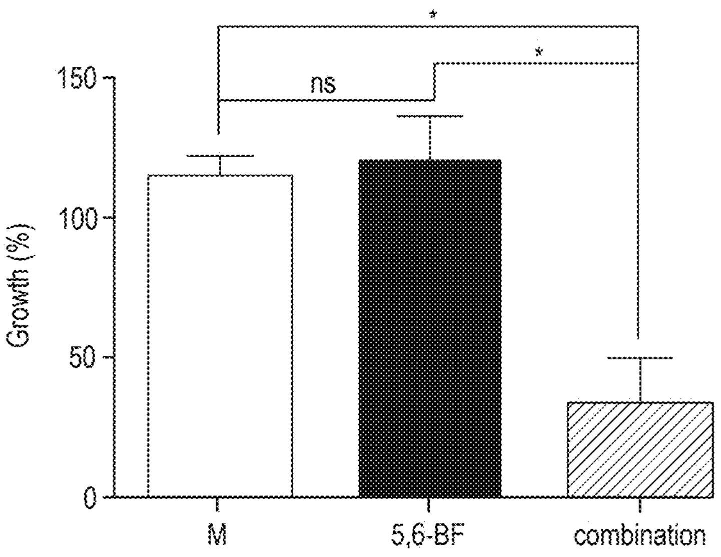
Figure 7D:
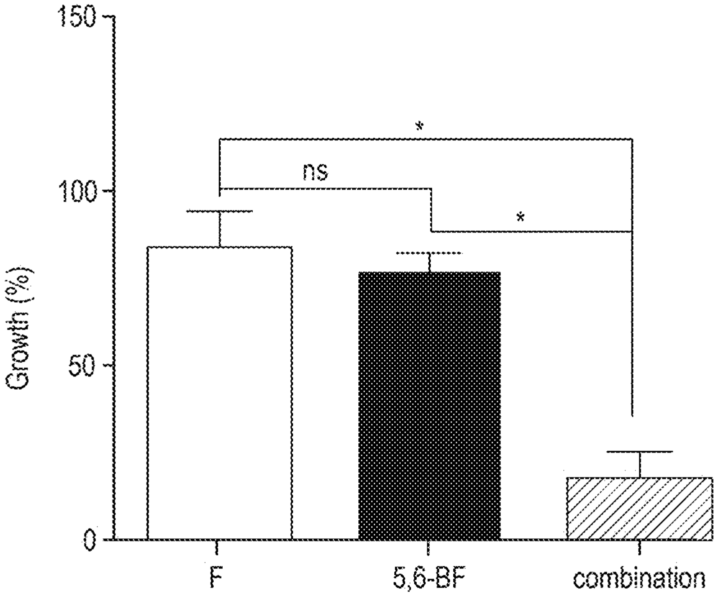

In vitro antifungal activity of 7,8-benzoflavone (7,8-BF) or 5,6-benzoflavone (5,6-BF) in combination with miconazole (M) or fluconazole (F) was analyzed by monitoring growth of yeast cells via $OD_{490}$ measurement, and the untreated control was set to 100%. In vitro antifungal activity of 7,8-BF or 5,6-BF in combination with M. *C. albicans* cells were either treated with 0.1 μM M or 12.5 μM flavone alone or in combination (see FIGS. 7A and C). In vitro antifungal activity of 7,8-BF or 5,6-BF in combination with F (see FIGS. 7B and D). *C. albicans* cells were either treated with 1 μM F or 25 μM flavone alone or in combination. Data represent means±SEM of at least 3 independent experiments. ns: not significant; *p<0.05; p<0.01; *p<0.001.

Figure 8A:
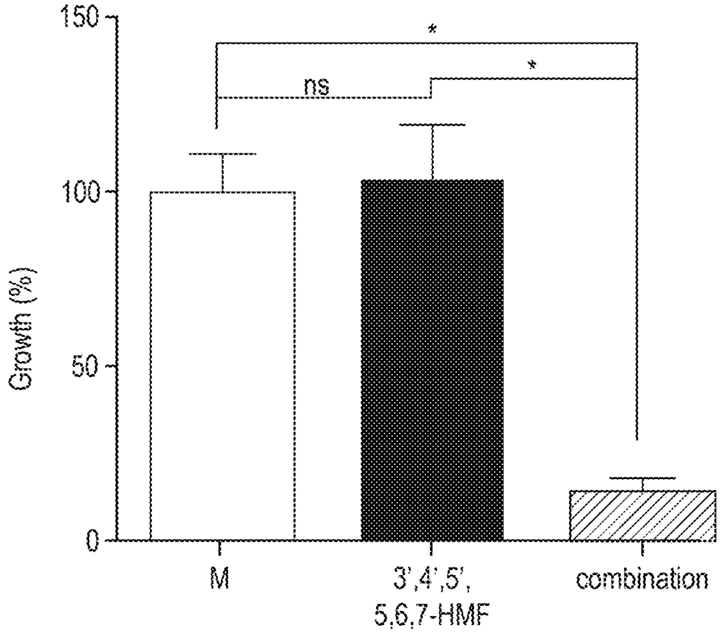
FIG. 8 shows the enhancement of the antifungal activity against *C. albicans* of azoles in the presence of 3',4',5',5,6,7-hexymethoxyflaovne (3',4',5',5,6,7-HMF) or 3',4',5,7-tetrametoxyflavone (3',4',5,7-TMF).
Figure 8B:
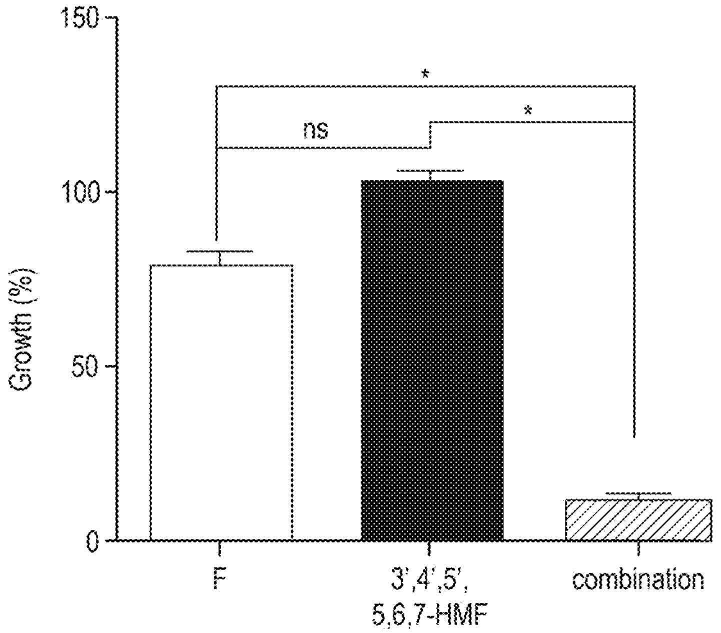
Figure 8C:
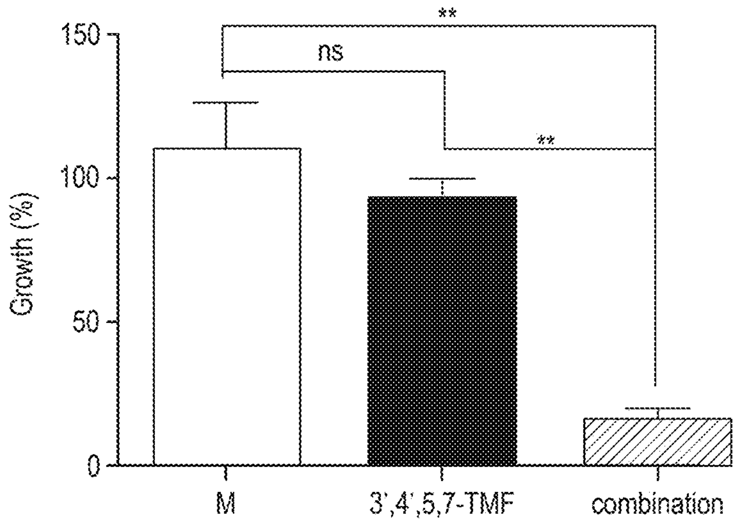
Figure 8D:
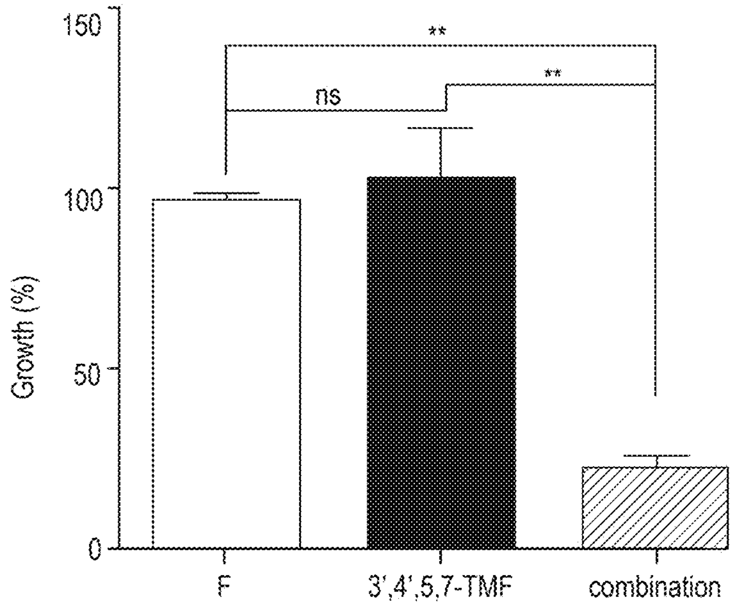

Example 8: Polymetoxylated Flavones Enhance the Antifungal Activity of Azole Antifungals In vitro antifungal activity of 3',4',5',5,6,7-hexymethoxyflaovne (3',4',5',5,6,7-HMF) or 3',4',5,7-tetrametoxyflavone (3',4',5,7-TMF) in combination with miconazole (M) or fluconazole (F) was analyzed by monitoring growth of yeast cells via $OD_{490}$ measurement, and the untreated control was set to 100%. In vitro antifungal activity of 3',4',5',5,6,7-HMF or 3',4',5,7-TMF in combination with M. *C. albicans* cells were either treated with 0.1 μM M or 12.5 μM (A)/6.25 μM (B) flavone alone or in combination (see FIGS. 8A and C). In vitro antifungal activity of 3',4',5',5,6,7-HMF or 3',4',5, 7-TMF in combination with F (see FIGS. 8B and D). *C. albicans* cells were either treated with 1 μM F or 6.25 μM (A)/12.5 μM (B) flavone alone or in combination. Data represent means±SEM of at least 3 independent experiments. ns: not significant; *p<0.05; **p<0.01.

Example 9: 5-MF Combination with Fluconazole Inhibits Biofilm Formation

The effect of 5-methoxyflavone (5-MF) in combination with fluconazole (Flu) on biofilm formation of *Candida albicans* was examined.

*Candida* biofilms were grown as described above and treated with either 5-MF (62.5 μM) or Flu (1 μM) alone or a combination of both. After 24 h of treatment, biofilms were washed once with PBS prior to dissolving biofilm cells carefully in 100 μL PBS. A dilution series of the re-suspended biofilm cells was then plated on YPD agar plates. YPD plates were incubated at 37° C. for 24 h hours and colony forming units (cfus) were counted.

Figure 9:
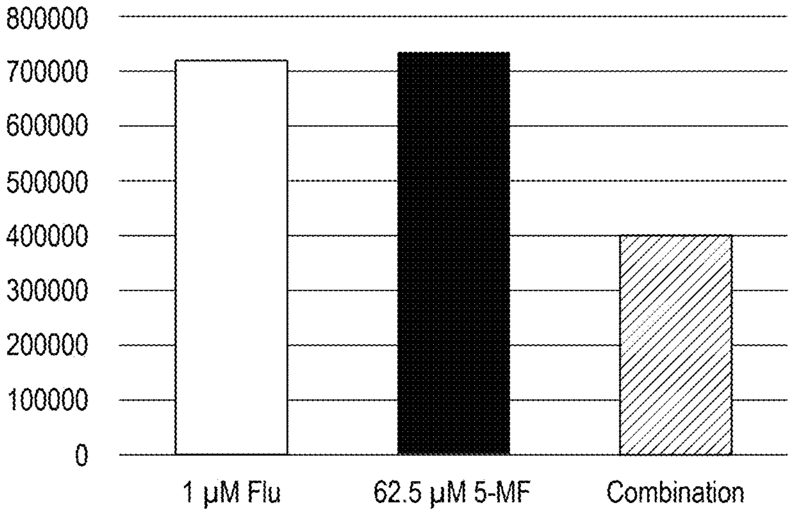
FIG. 9 shows that a combination of low concentrations of fluconazole (Flu) and 5-methoxyflavone (5-MF) drastically reduces biofilm formation of *Candida albicans*. The number of colony forming units (cufs) is significantly reduced compared to the separate application of Flu and 5-MF.

FIG. 9 shows that a combination of low concentrations of Flu and 5-MF drastically reduces the number of cufs compared to the individual application of Flu and 5-MF.

The invention claimed is:

1. A method of for inhibiting or preventing the growth of a fungal cell selected from the group consisting of *Cryptococcus fungi*, the method comprising contacting fungal cells with 5-methoxyflavone, in combination with fluconazole, both in an amount to exhibit a synergistic effect compared to the separate use of said 5-methoxyflavone and said fluconazole.

2. The method according to claim 1, wherein the fungal cell is a biofilm forming cell.

3. The method according to claim 1, wherein the fungal cell is selected from the group consisting of *Cryptococcus neoformans* and *Cryptococcus gattii.*

4. The method according to claim 1, wherein the 5-methoxyflavone is applied to a plant or parts thereof.

5. A method for treating a fungal infection in a human or animal caused by a fungus selected from the group consisting of *Cryptococcus fungi*, the method comprising administering to the human or animal of 5-methoxyflavone, wherein the 5-methoxyflavone is administered to the human or animal together or subsequently with fluconazole-2' methoxyflavone.

6. The method according to claim 5, wherein the 5-methoxyflavone and fluconazole are administered orally, topically, or intravenously.

7. A method for inhibiting or preventing the growth of a fungal cell comprising the step of contacting fungal cells with a composition comprising 5-methoxyflavone and fluconazole, both in an amount to exhibit a synergistic effect compared to the separate use of said 5-methoxyflavone and said fluconazole, with the proviso that the fungal cells are not *C. albicans.*

8. The method according to claim 4, wherein the plant or parts are selected from fruits or leaves.

9. The method according to claim 5, wherein the animal is a mammal.

10. The method according to claim 7, wherein the method is for treating a fungal infection in a human or animal caused by a fungus, the method comprising administering the composition to the human or animal.

11. The method according to claim 10, wherein the composition is administered orally, topically, or intravenously.

12. The method according to claim 10, wherein the animal is a mammal.

* * * * *